(12) United States Patent
Wright et al.

(10) Patent No.: US 9,334,252 B2
(45) Date of Patent: May 10, 2016

(54) PROCESS FOR PREPARING A DIVINYLARENE DIOXIDE

(71) Applicant: Blue Cube IP LLC, Midland, MI (US)

(72) Inventors: Robert J. Wright, Houston, TX (US); Kevin A. Frazier, Midland, MI (US); Gyongyi Gulyas, Lake Jackson, TX (US)

(73) Assignee: BLUE CUBE IP LLC, Midland, MI (US)

( * ) Notice: Subject to any disclaimer, the term of this patent is extended or adjusted under 35 U.S.C. 154(b) by 75 days.

(21) Appl. No.: 14/348,211

(22) PCT Filed: Oct. 16, 2012

(86) PCT No.: PCT/US2012/060327
§ 371 (c)(1),
(2) Date: Mar. 28, 2014

(87) PCT Pub. No.: WO2013/070392
PCT Pub. Date: May 16, 2013

(65) Prior Publication Data
US 2014/0256969 A1  Sep. 11, 2014

Related U.S. Application Data

(60) Provisional application No. 61/557,004, filed on Nov. 8, 2011.

(51) Int. Cl.
*C07D 301/12* (2006.01)
*C07D 303/04* (2006.01)

(52) U.S. Cl.
CPC ............ *C07D 301/12* (2013.01); *C07D 303/04* (2013.01)

(58) Field of Classification Search
CPC ....................................................... C07D 301/12
USPC ............................................................ 549/531
See application file for complete search history.

(56) References Cited

U.S. PATENT DOCUMENTS

| 8,497,387 | B2 | 7/2013 | Marks et al. | |
|---|---|---|---|---|
| 8,633,327 | B2 * | 1/2014 | Gulyas | C07D 301/12 549/526 |
| 8,669,384 | B2 * | 3/2014 | Ripplinger | C07D 301/03 549/524 |
| 8,674,122 | B2 * | 3/2014 | Ripplinger | C07D 301/12 549/523 |
| 8,716,503 | B2 * | 5/2014 | Gulyas | C07D 301/03 549/531 |

OTHER PUBLICATIONS

Inoue, et al. Effect of Anions on the Epoxidation of Styrenes with H2O2 in the Presence of Ammonium Heptamolybdate (VI)-Dioctyltin Oxide Catalysts. Bulletin of the Chemical Society of Japan. 1991. vol. 64, p. 3442-3444.

* cited by examiner

*Primary Examiner* — Golam M M Shameem

(57) ABSTRACT

A process for preparing a divinylarene dioxide including reacting (a) at least one divinylarene, (b) hydrogen peroxide, (c) at least one iron-containing catalyst, and (d) an excess of amine hydrogen halide, under conditions to form a divinylarene dioxide.

14 Claims, 2 Drawing Sheets

PROCESS FOR PREPARING A DIVINYLARENE DIOXIDE

FIELD

The present invention is related to a process for preparing a divinylarene dioxide. More specifically, the present invention relates to a process for preparing a divinylarene dioxide by epoxidizing a divinylarene with hydrogen peroxide and an iron-containing catalyst capable of providing an increased yield of a divinylarene dioxide product.

Divinylarene dioxides, for example divinylbenzene dioxide (DVBDO) and others which are derived from divinylbenzene (DVB) are a class of diepoxides which can be used as either a reactive diluent or as the main epoxy resin matrix in an epoxy thermoset formulation. DVBDO itself has a very low liquid viscosity (for example less than about 20 centipoises (0.02 Pa-s) making DVBDO especially useful in the preparation of low viscosity epoxy formulations. The epoxy formulations made from DVBDO are useful as intermediates in the production of various other products. For example, epoxy formulations made from DVBDO are suitable for use in the fields of coatings, composites, and molding compositions.

The preparation of divinylarene dioxides, for example DVBDO, typically involves the epoxidation of divinylarene such as DVB. Epoxidation of divinylarene, such as DVB, presents several challenges in an industrial process for making divinylarene dioxide, such as DVBDO, because the divinylarene contains two terminal olefin groups in the molecule as compared with mono-olefins. If some of the olefin groups of a diolefin compound are not converted to epoxides (for example as shown in the simplified Reaction Scheme I below with m-DVB) a monoxide such as divinylbenzene monoxide (DVBMO) would remain in the resultant crude product.

Reaction Scheme I

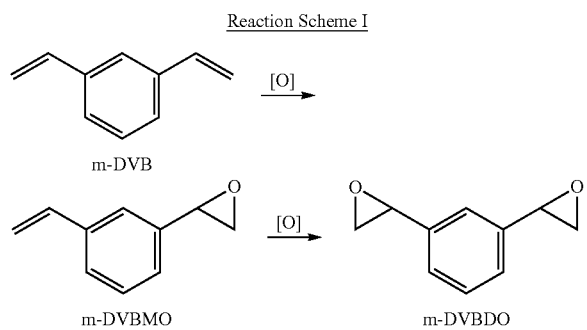

The boiling points of the undesired monoxide such as DVBMO and the desired dioxide product such as DVBDO are so close to each other that a highly efficient separation method would be required to remove the undesired DVBMO from the desired product DVBDO, thus increasing the cost and complexity of the process for producing DVBDO on an industrial scale. DVB and DVBMO are also prone to polymerization which adds to the complexity of the process.

Heretofore, the epoxidation of DVB using hydrogen peroxide and a metal catalyst has been disclosed in the art. For example, Inoue et al (*Bull. Chem. Soc. Jpn.*, 1991, 64, 3442) discloses the preparation of DVBDO by reacting hydrogen peroxide ($H_2O_2$) with DVB in the presence of a molybdenum (Mo) catalyst. The yield of DVBDO disclosed in the above reference is just 10 percent (%) because of product instability and catalyst decomposition. Another process disclosed in JP 09286750 produces DVBDO in a 30% yield. The following four other processes are disclosed in WO 2010-077483 A1 for the synthesis of DVBDO: (1) methyltrioxorhenium (MTO) and $H_2O_2$; (2) ammonium salts of peroxophosphatetungstic acid and $H_2O_2$; (3) $FeCl_3.6H_2O$, $H_2$Pydic (pyridine-2,6-dicarboxylic acid), and an amine with $H_2O_2$; and (4) Mn(III) HQ complexes, ammonium acetate, acetic acid and $H_2O_2$.

The synthesis of DVBDO using MTO and hydrogen peroxide produces DVBDO in a 70% yield. However, MTO is expensive and its use on an industrial scale can be cost prohibitive. The use of the less expensive peroxophosphatetungstic acid catalyst and Mn(III) HQ catalyst produces DVBDO in a 20% yield and an 18% yield, respectively.

The mixture composed of $FeCl_3·6H_2O$, $H_2$Pydic, and an amine with $H_2O_2$ produces DVBDO in a 77% yield; however, 1% to 3% divinylbenzene monooxide (DVBMO) is still present in the mixture. DVBMO is a less desirable co-product; and separation of any remaining amount of DVBMO from DVBDO product is difficult. In addition, the process requires a 5% loading of Fe; because heretofore, it is known that a catalyst loading of less than 5 mol % does not provide DVBDO yields over 77%. Furthermore, the process only uses a DVB loading of 0.76% by volume. In other words, dilute solutions of DVB must be used, which is far from ideal for an industrial process. In addition, the process requires 2 equivalents of hydrogen peroxide for every vinyl group. Therefore, double the theoretical amount of hydrogen peroxide is required, which is wasteful and costly.

SUMMARY

The present invention is directed to a process for preparing a divinylarene dioxide; and more specifically the present invention is directed to a process for preparing a divinylarene dioxide by a catalytic reaction of a divinylarene and a hydrogen peroxide oxidant in the presence of an iron-containing catalyst and in the presence of an amine hydrogen halide.

In one embodiment, the present invention includes a process for preparing a divinylarene dioxide by reacting (a) at least one divinylarene, (b) hydrogen peroxide as an oxidant, (c) at least one iron-containing catalyst, and (d) at least one equivalent of an amine hydrogen halide (relative to the iron catalyst) under conditions to form a divinylarene dioxide.

For example, in one preferred embodiment, the present invention provides a metal catalyzed route to DVBDO starting from DVB, hydrogen peroxide, an iron-containing catalyst and an amine hydrogen halide; wherein the amount of undesirable co-products produced is low (generally less than 5%). In addition to producing low amounts of undesirable co-products, the process of the present invention has other advantages including for example the following: (1) the metal is readily available and relatively inexpensive; (2) the yield of DVBDO is at least about 77%; (3) a mixed tertiary alcohol and chlorinated solvent is employed; (4) the catalyst loading is low (about 2.5 mol % or lower); (5) the equivalents of hydrogen peroxide per vinyl group is low (e.g., less than about 2 and approaches about 1); (6) the loading of DVB is at least about 1% by volume; and (7) the reaction is fast, e.g., the reaction is completed in less than about 4 hours.

In one embodiment, the iron-containing catalyst used in the process of the present invention may include for example Fe compounds containing Pydic (pyridine-2,6-dicarboxylate) ligands or mixtures made from $FeCl_3·6H_2O$, $H_2$Pydic (pyridine-2,6-dicarboxylic acid) which meet all of the above advantages (1)-(7) when at least an equivalent of amine hydrogen halide is added to the reaction mixture. It has been found that without the addition of an amine hydrogen halide (e.g., diisopropylamine HCl), the yield of DVBDO is lower than about 41%.

For example, to illustrate one embodiment, the yield of DVBDO with a 2.5 mol % loading of PydicFeCl(OH$_2$)$_2$ in a formulation is only 4.4%; but when about 10 mol % of diisopropylamine HCl is added to the formulation, the yield dramatically increases to about 87.3%. It has also been found that the addition of about 3.1 mol % of diisopropylamine HCl to an in-situ generated catalyst (about 0.31 mol % Fe) mixture affords about 85.6% yield of DVBDO. Without the addition of diisopropylamine HCl to the reaction composition, the yield of DVBDO is only about 41.4% with about 52.4% of DVBMO remaining.

DETAILED DESCRIPTION

Figure 1:
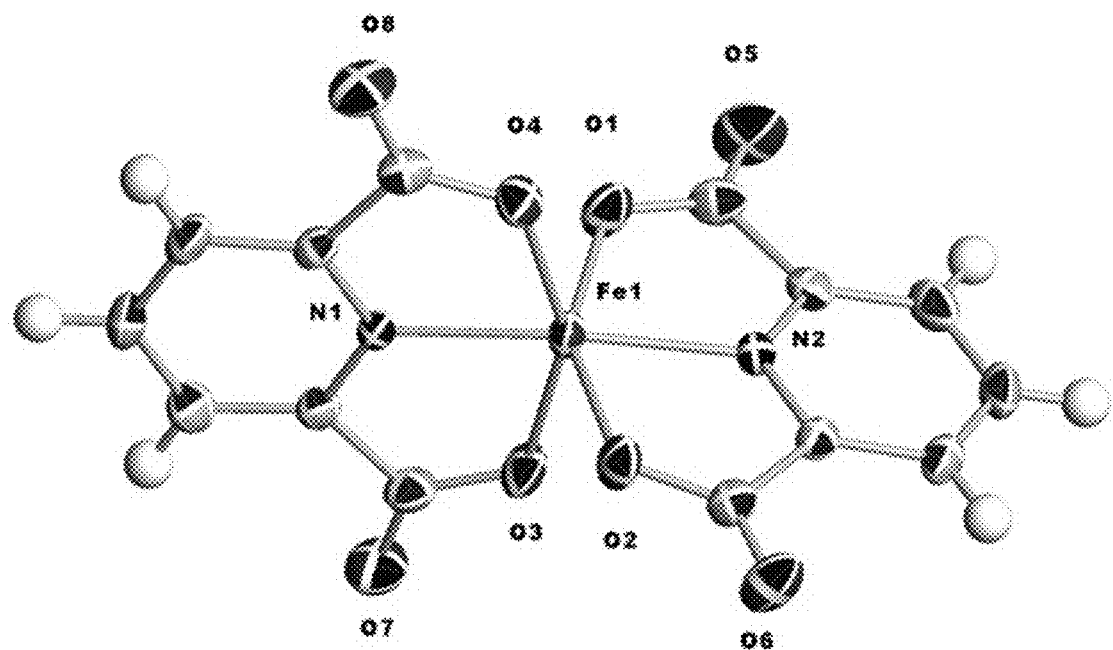
FIG. 1 is a thermal ellipsoid plot of [Fe(Pydic)$_2$][NH$_2$(isopropyl)$_2$], where the diisopropylammonium cations were removed for clarity.
Figure 2:
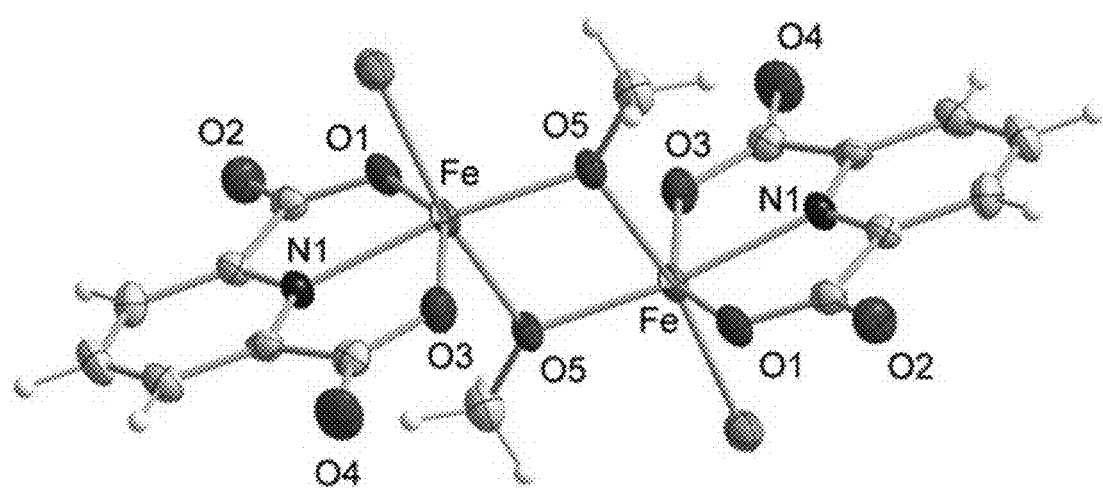
FIG. 2 is a thermal ellipsoid plot of [(PydicFe(OMe)Cl)$_2$]2[NH$_2$(isopropyl)$_2$], where the diisopropylammonium cations were removed for clarity.

In its broadest scope, the present invention includes a process for preparing a divinylarene dioxide from a divinylarene using hydrogen peroxide as an oxidant in the presence of a catalyst, particularly an iron-containing catalyst; and in the presence of an amine additive such as amine hydrogen halide; and other optional additives such as a solvent; wherein that the resulting divinylarene dioxide product produced by the above reaction process is substantially free of remaining DVB and/or DVBMO. "Substantially free of remaining DVB and/or DVBMO" as used in reference to a reaction product herein means for DVB substantially free is less than about 1% and for DVBMO substantially free is less than about 5%.

In accordance with one embodiment of the present invention, the process of epoxidizing divinylarene compounds to obtain divinylarene dioxide compounds may be carried out by reacting together the following compounds: (a) at least one divinylarene, (b) a sufficient amount of hydrogen peroxide as an oxidant, (c) at least one iron-containing catalyst, and (d) at least 1 equivalent of amine hydrogen halide relative to the iron (Fe) element of the iron-containing catalyst.

The source of divinylarene useful in the present invention may come from any known sources and particular to known processes for preparing divinylarenes. For example, divinylarenes can be prepared with salt or metal wastes from arenes and ethylene.

In one embodiment of the present invention, the divinylarene useful in the present invention may comprise any substituted or unsubstituted arene nucleus bearing two vinyl groups in any ring position. The arene may include for example benzene, substituted benzenes, or (substituted) ringannulated benzenes, and mixtures thereof. In one embodiment, divinylbenzene may be ortho, meta, or para isomers or any mixture thereof. Additional substituents may consist of oxidation-resistant groups including for example saturated alkyl, aryl, halogen, nitro, isocyanate, or RO— (where R may be saturated alkyl or aryl), or mixtures thereof. Ring-annulated benzenes may include for example naphthalene, tetrahydronaphthalene, and the like, and mixtures thereof.

In another embodiment, the divinylarene may contain quantities of substituted arenes. The amount and structure of the substituted arenes depend on the process used in the preparation of the divinylarene. For example, DVB prepared by a known dehydrogenation of diethylbenzene (DEB) may contain ethylvinylbenzene (EVB) and DEB.

The divinylarene used in the process of the present invention may include for example divinylbenzene, divinylnaphthalene, divinylbiphenyl, divinyldiphenylether, and mixtures thereof.

The concentration of the divinylarene used in the present invention may range generally from about 0.5 weight percent (wt %) to about 50 wt % in one embodiment, from about 1 wt % to about 10 wt % in another embodiment, and from about 2 wt % to about 8 wt % in still another embodiment, based on the total weight of the composition.

The oxidizing agent or oxidant useful in the present invention includes hydrogen peroxide. Generally, the molar ratio of hydrogen peroxide:divinylarene useful in the present invention may be up to about 5:1 in one embodiment, and may range from about 1:1 to about 5:1 in another embodiment, from about 1:1 to about 4:1 in still another embodiment, and from about 1:1 to about 3:1 in yet another embodiment.

The preparation of divinylarene dioxides using hydrogen peroxide as the oxidant is achieved with the use of an iron-containing catalyst. The iron-containing catalyst may include for example an iron salt and a chelating ligand. The iron salt can be for example Fe(II) chloride or bromide or acetate and the like or mixtures thereof; or Fe(III) fluoride, chloride, bromide, acetate, and the like or mixtures thereof. The chelating ligand may include for example alkyl- or aryl-substituted formamidines; alkyl-, aryl-, aralkyl-, halogen-, carboxylic acid-, and amino-substituted N-heterocycles such as imidazole, pyrazole, pyridine, oxazole, thiazole; amino acids; and mixtures thereof. For the purpose of illustrating several embodiment of the present invention, the following chemical structures show a form of the present invention. However, it should be understood that the present invention is not limited to the embodiments shown in the following chemical structures which shows the H$_2$Pydic ligand and some of its possible derivative:

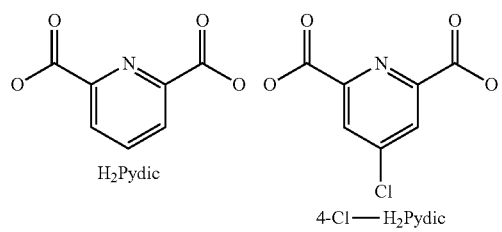

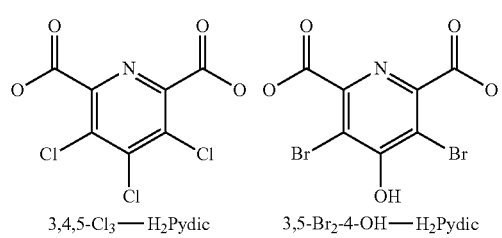

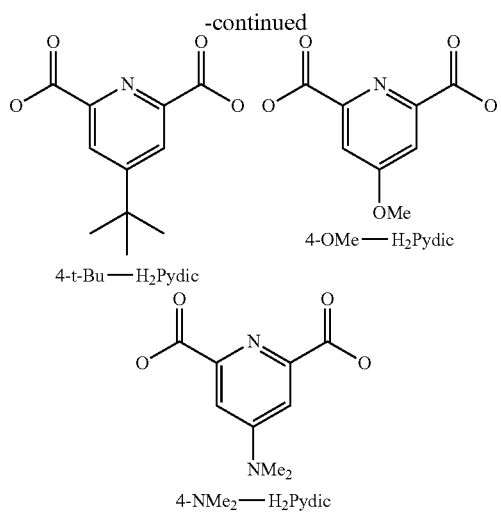

4-t-Bu—H₂Pydic

4-OMe—H₂Pydic

4-NMe₂—H₂Pydic

The catalyst can be in-situ generated in the reaction mixture or the catalyst may be isolated and added to the reaction mixture.

The concentration of the iron-containing catalyst use in the reactive composition may include in general from about 0.001 mol % to about 20 mol % in one embodiment, from about 0.01 mol % to about 10 mol % in another embodiment; from about 0.1 mol % to about 5 mol % in still another embodiment; and from about 0.5 mol % to about 2.5 mol % in yet another embodiment. In one other embodiment, the loading of the iron-containing catalyst ranges from about 0.3 mol % to about 2.5 mol % of the divinylarene.

The amine hydrogen halide useful in the present invention include compounds of the general formula [NHR$_3$][X], [NH$_2$R$_2$][X], and [NH$_3$R][X], which are amine hydrogen halides composed from tertiary, secondary, and primary amines. Group R may be broadly defined as alkyl or aryl. More specifically the amines used may be aliphatic, arylalkyl or cycloaliphatic amines and amino acids; and mixtures thereof. Aliphatic amines may include, for example, primary and secondary amines such as propyl amine, isopropyl amine, diisopropylamine; and mixtures thereof. The arylalkyl amines may include for example benzyl amine. The cycloaliphatic amines may include for example cyclohexylamine. The amino acids may include for example histidine. The halide or pseudohalide X may be F, Cl, Br, I, trifluoromethanesulfonate (triflate), and p-toluenesulfonate (tosyl).

The concentration of the amine hydrogen halide used in the reactive composition may include in general from about 0.001 mol % to about 100 mol % in one embodiment, from about 0.01 mol % to about 50 mol % in another embodiment; from about 0.1 mol % to about 25 mol % in still another embodiment; and from about 1 mol % to about 12.5 mol % in yet another embodiment.

A solvent may be optionally added to the reactive composition used in the process of the present invention. The optional solvent useful in the process of the present invention may include for example any inert organic solvent that is inert to the oxidant under the reaction conditions. For example, the solvent may include halogenated alkanes such as dichloromethane; aromatics such as toluene; polar organic solvents such as dimethylformamide, acetonitrile, or ethers such as tetrahydrofuran; alcohols such as tert-amyl alcohol, tert-butanol, or methanol; fluorinated alcohols such as trifluoroethanol; or ketones, such as acetone or methyl-ethyl ketone or mixtures thereof.

The concentration of the optional solvent used in the present invention may range generally from 0 wt % to about 99 wt % in one embodiment, from about 10 wt % to about 90 wt % in another embodiment, and from about 20 wt % to about 80 wt % in still another embodiment.

An assortment of other optional additives known in the art may be added to the reaction composition of the present invention including for example, other resins, stabilizers, fillers, plasticizers, catalyst de-activators, and the like; and mixtures thereof.

The concentration of the optional additives used in the present invention may range generally from 0 wt % to about 99.9 wt % in one embodiment, from about 0.1 wt % to about 99.9 wt % in another embodiment, from about 1 wt % to about 99 wt % in still another embodiment, and from about 2 wt % to about 98 wt %, in yet another embodiment, base on the weight of all the components in the composition.

The preparation of divinylarene dioxides may be achieved for example by (i) adding to a reactor the following reactants: a divinylarene, an iron-containing catalyst, an amine hydrogen halide, and optionally an inert organic solvent; (ii) contacting the reactants with an oxidant; and then (iii) allowing the components in the reaction mixture to react under reaction conditions to produce the corresponding divinylarene dioxide.

The reaction conditions include carrying out the reaction under a temperature, generally in the range of from about 0° C. to about 100° C. in one embodiment, from about 5° C. to about 80° C. in another embodiment, and from about 20° C. to about 60° C. in still another embodiment.

The pressure of the reaction may be generally from about 10.13 kPa to about 1013 kPa (0.1 atmosphere (atm) to about 10 atm).

The reaction process of the present invention may be a batch or a continuous process. The reactor used in the process may be any reactor and ancillary equipment well known to those skilled in the art.

After the reaction of the present invention, the undesirable by-products; and any remaining amine hydrogen halide, catalyst, and solvent, may be removed to recover a sufficient amount of usable divinylarene dioxide product. The resulting divinylarene dioxide reaction product can be isolated by any known means. Then the product may optionally be purified by well-known means in the art such as by chromatography, distillation, crystallization, and the like. Preferably, the isolated divinylarene dioxide reaction product is purified by a distillation process.

One advantage of the present invention process is that high yields of divinylarene dioxides may be produced by the process of the present invention. With high yields of divinylarene dioxides produced, the process of the present invention advantageously requires less recycle and produces less waste.

The "high yield" of divinylarene dioxide produced by the process of the present invention is generally greater than about 77% in one embodiment, from about 85% to about 100% in another embodiment; from about 90% to about 100% in still another embodiment, and from about 95% to about 100% in yet another embodiment, based on divinylarene starting material.

The divinylarene dioxides prepared by the process of the present invention, particularly those derived from divinylbenzene such as for example divinylbenzene dioxide (DVBDO), are class of diepoxides which have a relatively low liquid viscosity but a higher rigidity than conventional epoxy resins.

The divinylarene dioxide prepared by the process of the present invention may comprise, for example, any substituted or unsubstituted arene nucleus bearing two vinyl groups in any ring position. The arene portion of the divinylarene dioxide may consist of benzene, substituted benzenes, or (substituted) ring-annulated benzenes or homologously bonded (substituted) benzenes, or mixtures thereof. The divinylarene portion of the divinylarene dioxide may be ortho, meta, or para isomers or any mixture thereof. Additional substituents may consist of oxidant-resistant groups including saturated alkyl, aryl, halogen, nitro, isocyanate, or R'O— wherein R' may be the same as defined above. Ring-annulated benzenes may consist of naphthlalene, tetrahydronaphthalene, and the like. Homologously bonded (substituted) benzenes may consist of biphenyl, diphenylether, and the like.

The divinylarene dioxide product prepared by the process of the present invention may be illustrated generally by general chemical Structures V-VIII as follows:

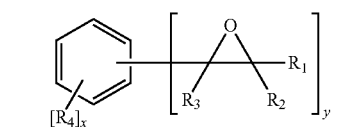

Structure V

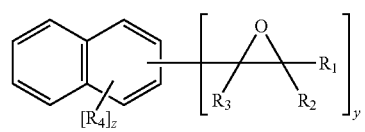

Structure VI

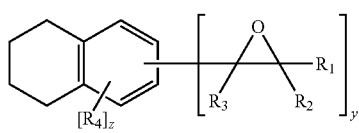

Structure VII

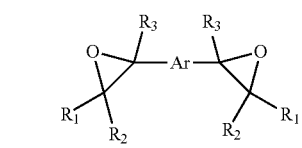

Structure VIII

In the above Structures V, VI, VII and VIII of the divinylarene dioxide product of the present invention, each $R_1$, $R_2$, $R_3$ and $R_4$ individually may be hydrogen, an alkyl, cycloalkyl, an aryl or an aralkyl group, where the alkyl, cycloalkyl, aryl, and aralkyl groups may have from 1 to about 18 carbon atoms in one embodiment and from 1 to 4 carbon atoms in another embodiment; or a oxidant-resistant group including for example a halogen, a nitro, an isocyanate, or an R'0 group, wherein R' may be an alkyl, aryl or aralkyl group having from 1 to about 18 carbon atoms in one embodiment and from 1 to 4 carbon atoms in another embodiment; x may be an integer of 0 to 4; y may be an integer greater than or equal to 2; x+y may be an integer less than or equal to 6; z may be an integer of 0 to 6; z+y may be an integer less than or equal to 8; and Ar is an arene fragment including for example, 1,3-phenylene group.

The divinylarene dioxide product produced by the process of the present invention may include for example alkyl-vinylarene monoxides depending on the presence of alkyl-vinylarene in the starting material. The structure of the divinylarene dioxide, and composition of structural isomers, is determined by the divinylarene feedstock used. The reaction to epoxidize the ethylenic bonds do not generally impact the isomer distribution of the reactants as they are converted.

In one embodiment of the present invention, the divinylarene dioxide produced by the process of the present invention may include for example divinylbenzene dioxide, divinylnaphthalene dioxide, divinylbiphenyl dioxide, divinyldiphenylether dioxide, and mixtures thereof.

In a preferred embodiment of the present invention, the divinylarene dioxide used in the epoxy resin formulation may be for example DVBDO. In another preferred embodiment, the divinylarene dioxide component that is useful in the present invention includes, for example, a DVBDO as illustrated by the following chemical formula of Structure IX:

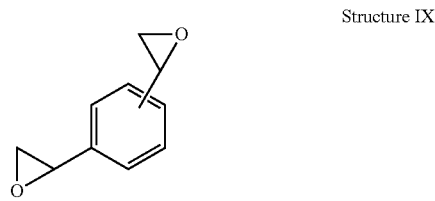

Structure IX

The chemical formula of the above DVBDO compound may be as follows: $C_{10}H_{10}O_2$; the molecular weight of the DVBDO is about 162.2; and the elemental analysis of the DVBDO is about: C, 74.06; H, 6.21; and O, 19.73 with an epoxide equivalent weight of about 81 g/mol.

Divinylarene dioxides, particularly those derived from divinylbenzene such as for example DVBDO, are class of diepoxides which have a relatively low liquid viscosity but a higher rigidity and crosslink density than conventional epoxy resins.

Structure X below illustrates an embodiment of a preferred chemical structure of the DVBDO useful in the present invention:

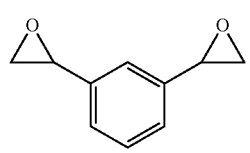

Structure X

Structure XI below illustrates another embodiment of a preferred chemical structure of the DVBDO useful in the present invention:

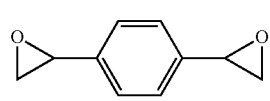

Structure XI

When DVBDO is prepared by the process of the present invention, it may be possible to obtain one of three possible isomers: ortho, meta, and para. Accordingly, the present invention includes a DVBDO illustrated by any one of the above structures individually or as a mixture thereof. Structures X and XI above show the meta (1,3-DVBDO) isomer of DVBDO and the para (1,4-DVBDO) isomer of DVBDO, respectively. The ortho isomer is rare; and usually DVBDO is mostly produced generally in a range of from about 9:1 to about 1:9 ratio of meta isomer (Structure X) to para isomer (Structure XI). The present invention preferably includes as one embodiment a range of from about 6:1 to about 1:6 ratio of Structure X to Structure XI, and in other embodiments the ratio of Structure X to Structure XI may be from about 4:1 to about 1:4 or from about 2:1 to about 1:2.

The structure of the divinylarene dioxide, and composition of structural isomers, is determined by the divinylarene feedstock used. In one embodiment, divinylbenzene feedstock contains a meta:para ratio of generally in a range of from about 9:1 to about 1:9. In another embodiment, the divinylbenzene feedstock may be from about 6:1 to about 1:6; from about 4:1 to about 1:4 in yet another embodiment; from about 2.5:1 to about 1:2.5 in still another embodiment; or from about 1.5:1 to about 1:1.5 another embodiment. In a preferred embodiment, the meta:para ratio of the divinylbenzene and the divinylbenzene dioxide both may range from about 9:1 to about 1:9 ratio; and in another embodiment, the meta:para ratio of the divinylbenzene and the divinylbenzene dioxide both may range from about 2.5:1 to abut 1:2.5 ratio.

The feedstock may also contain impurities including, but not limited to, ethylvinylbenzene (EVB), naphthalene, polyethylbenzenes (e.g. diethylbenzene, triethylbenzene, tetraethylbenzene, pentaethylbenzene, diphenylethane, other alkylated benzenes, and higher molecular weight oils), free radical inhibitors, or mixtures thereof. The divinylbenzene content of the feed may be greater than 55% in one embodiment; greater than 63% in another embodiment; greater than 80% in still another embodiment; greater than 90% in still another embodiment; or greater than 95% in yet another embodiment. The amount of co-product EVBO that is produced and that must be separated to obtain higher purity DVBDO is determined by DVB feed stock composition. In one preferred embodiment, the divinylarene feed stock purity may be greater than about 80 percent.

In one embodiment, the process of the present invention may be particularly suited for the preparation of divinylbenzene dioxide, a low viscosity liquid epoxy resin. The viscosity of the divinylarene dioxides produced by the process of the present invention ranges generally from about 10 mP-s to about 100 mP-s at 25° C. in one embodiment; from about 10 mP-s to about 50 mP-s at 25° C. in another embodiment; and from about 10 mP-s to about 25 mP-s at 25° C. in still another embodiment.

The utility of the divinylarene dioxides of the present invention requires thermal stability to allow formulating or processing the divinylarene dioxides at moderate temperatures (for example, at temperatures of from about 100° C. to about 200° C.) for up to several hours (for example, for at least 2 hours or more) without oligomerization or homopolymerization. Oligomerization or homopolymerization during formulation or processing is evident by a substantial increase (e.g., greater than 50 fold) in viscosity or gelling (crosslinking). The divinylarene dioxides of the present invention have sufficient thermal stability such that the divinylarene dioxides do not experience a substantial increase in viscosity or gelling during formulation or processing at the aforementioned moderate temperatures.

The divinylarene dioxide products of the present invention are useful for the preparation of epoxy resin compositions or formulations which, in turn, are useful for preparing thermosets or cured products in the form of coatings, films, adhesives, laminates, composites, electronics, and the like.

EXAMPLES

The following examples and comparative examples further illustrate the present invention in detail but are not to be construed to limit the scope thereof.

In the Examples, various terms and designations are used such as the following:
 "DVB" stands for divinylbenzene.
 "DVBDO" stands for divinylbenzene dioxide.
 "DVBMO" stands for divinylbenzene monooxide.
 "$H_2$Pydic" stands for pyridine-2,6-dicarboxylic acid.
 "Pydic" stands for pyridine-2,6-dicarboxylate.

In the following Examples, products were analyzed by standard gas chromatography (GC) analytical equipment.

All chemicals used in the Examples, unless specified, were purchased from Sigma-Aldrich and used without further purification.

PydicFeCl(OH$_2$)$_2$ (*Inorg. Chem.* 1995, 34, 5156) and [PydicFe(OH)(OH$_2$)]$_2$ (*J. Am. Chem. Soc.* 1976, 98(6), 1425) were synthesized according to the above literature procedures.

Catalyst Synthesis Example 1

This catalyst synthesis example illustrates a method for preparing an epoxidation catalyst and a method for isolating the catalyst. FeCl$_3$.6H$_2$O (1.076 g, 4 mmol) and H$_2$Pydic (0.668 g, 4 mmol) were charged in a 300 mL round bottomed flask along with MeOH (200 mL). The mixture was stirred for 5 minutes (min) to afford a yellow solution. Diisopropylamine (8 mmol, 0.808 g, 1.13 mL) was added and the solution was placed in a 50° C. oil bath for 45 min. The solution was concentrated to 15 mL under reduced pressure. X-ray quality crystals were grown by the following vapor diffusion method: The solution was placed in a 30 mL vial that was placed inside a 100 mL vial that contained 30 mL of Et$_2$O. The 100 mL jar was tightly sealed. Both blue-green catalyst crystals of [Fe(Pydic)$_2$][NH$_2$(isopropyl)$_2$] (0.400 g, 36.1% based on iron) and yellow catalyst crystals of [(PydicFe(OMe)Cl)$_2$]2[NH$_2$(isopropyl)$_2$] (0.095 g, 8.8% based on iron) grew overnight. The chemical formulas and structures of both [Fe(Pydic)$_2$][NH$_2$(isopropyl)$_2$] and [(PydicFe(OMe)Cl)$_2$]2[NH$_2$(isopropyl)$_2$] were determined by X-ray crystallography. The unit cell parameters for both crystals are as follows:

| Crystallographic Data for Fe(Pydic)$_2$][NH$_2$(isopropyl)$_2$] and [(PydicFe(OMe)Cl)$_2$]2[NH$_2$(isopropyl)$_2$] | | |
|---|---|---|
| | [Fe(Pydic)$_2$][NH$_2$(isopropyl)$_2$] (1) | [(PydicFe(OMe)Cl)$_2$]2[NH$_2$(isopropyl)$_2$] (2) |
| Formula | C$_{9.50}$H$_{8.50}$FeN$_3$O$_4$ | C$_7$H$_{11}$Cl$_{0.5}$Fe$_{0.5}$NO$_{2.5}$ |
| Formula Weight (Fw) | 284.54 | 194.82 |
| Crystal system | Triclinic | Triclinic |
| Space group | P$_{\bar{1}}$ | P$_{\bar{1}}$ |
| a, Å | 7.8020(12) | 8.239(2) |
| b, Å | 10.2341(14) | 10.765(3) |
| c, Å | 14.335(2) | 11.461(3) |
| A | 91.195(4)° | 101.634(9)° |
| B | 97.947(4)° | 107.271(8)° |
| C | 105.144(4)° | 106.035(9)° |

-continued

| Crystallographic Data for Fe(Pydic)$_2$][NH$_2$(isopropyl)$_2$] and [(PydicFe(OMe)Cl)$_2$]2[NH$_2$(isopropyl)$_2$] | | |
|---|---|---|
| | [Fe(Pydic)$_2$][NH$_2$(isopropyl)$_2$] (1) | [(PydicFe(OMe)Cl)$_2$]2[NH$_2$(isopropyl)$_2$] (2) |
| V, Å$^3$ | 1092.3(3) | 887.2(4) |
| Z | 4 | 4 |
| d$_{calc}$, g cm$^{-3}$ | 1.730 | 1.458 |
| μ, mm$^{-1}$ | 1.389 | 1.024 |
| R$_1$ [I > 2σ(I)] | 0.0399 | 0.0775 |
| wR$_2$, (all data) | 0.0900 | 0.2198 |

Catalyst Synthesis Example 2

This catalyst synthesis example illustrates an alternative and higher yielding synthesis for [(PydicFe(OMe)Cl)$_2$]2 [NH$_2$(isopropyl)$_2$]. [PydicFeOH(OH$_2$)]$_2$ (0.256 g, 0.5 mmol) and diisopropylamine HCl (0.138 g, 1 mmol) were added together in a 100 mL round bottomed flask with MeOH (75 mL). The mixture was refluxed for 2 hours (hr) and the resulting yellow solution was concentrated to 20 mL and filtered. Crystals of [(PydicFe(OMe)Cl)$_2$]2[NH$_2$(isopropyl)$_2$]_(0.270 g, 69% yield) were grown overnight by the vapor diffusion of Et$_2$O into the MeOH solution.

Epoxidation Example 1

Increased Yield of DVBDO in a Mixed Solvent

FeCl$_3$.6H$_2$O (16.9 mg, 0.0625 mmol) and H$_2$Pydic (10.45 mg, 0.0625 mmol) were charged into a 50 mL round bottomed flask and MeOH (10 mL) was added. The mixture was stirred for 2 min to afford a pale yellow solution. Diisopropylamine (12.7 mg, 0.125 mmol) was added dropwise over 30 seconds (s) and the mixture was placed in a 50° C. oil bath for 30 min. The solvent was removed under reduced pressure to afford a yellow residue. It was dissolved in 1:2: CH$_2$Cl$_2$:t-amylOH to a final volume of 37.5 mL. To the stirred mixture DVB (2.5 mmol) was added followed by the dropwise addition of H$_2$O$_2$ (10 mmol as a 30% solution in water) over 5 min. The reaction mixture was analyzed by GC-MS after 2 hr resulting in 100% DVB conversion, no DVBMO was detected and the DVBDO yield was 93%.

Epoxidation Example 2

The reaction was carried out as described in Epoxidation Example 1 but instead of using 1:2: CH$_2$Cl$_2$:t-amylOH solvent mixture, 1:2: CH$_2$Cl$_2$:t-butylalcohol mixture was used. The results are summarized in Table I.

Comparative Epoxidation Example A

The reaction was carried out as described in Epoxidation Example 1 but instead of using 1:2: CH$_2$Cl$_2$:t-amylOH solvent mixture, only t-amylOH was used. The results are summarized in Table I.

Comparative Epoxidation Example B

The reaction was carried out as described in Epoxidation Example 1 but instead of using 1:2: CH$_2$Cl$_2$:t-amylOH solvent mixture, only t-butyl alcohol was used. The results are summarized in Table I.

TABLE I

Results of DVBDO Formation as a Function of Solvent

| Example | Solvent or Solvent Blend | Time, hr | % Conversion of DVB | GC Area % DVBMO | GC Area % DVBDO | GC Area % By-product |
|---|---|---|---|---|---|---|
| Epoxidation 1 | 1:2: CH$_2$Cl$_2$:t-amylOH | 2 | 100 | 0 | 93.0 | 7.0 |
| Epoxidation 2 | 1:2: CH$_2$Cl$_2$:t-butylOH | 2 | 100 | 0 | 92.8 | 7.2 |
| Comparative A | t-amyl alcohol | 2 | 100 | 11.4 | 77.4 | 11.2 |
| Comparative B | t-butyl alcohol | 2 | 100 | 19.3 | 72.2 | 8.5 |

Epoxidation Examples 1 and 2 illustrate that upon using a mixed solvent composed of approximately ⅓ CH$_2$Cl$_2$ and ⅔ either t-amylOH or t-butylOH, the yield of DVBDO is greater than 77% (the greatest yield reported in WO 2010-077483 A1) and that there is no remaining DVBMO.

Epoxidation Example 3

In this example, a high yield of DVBDO was obtained with 1.5 equivalents of hydrogen peroxide in a mixed solvent. FeCl$_3$.6H$_2$O (33.8 mg, 0.125 mmol) and H$_2$Pydic (20.9 mg, 0.125 mmol) were charged into a 100 mL round bottomed flask and MeOH (20 mL) was added. The mixture was stirred for 2 min to afford a pale yellow solution. Diisopropylamine (25.3 mg, 0.250 mmol) was added dropwise over 30 s and the mixture was placed in a 50° C. oil bath for 30 min. The solvent was removed under reduced pressure to afford a yellow residue. It was then dissolved in CH$_2$Cl$_2$ (25 mL) and t-amylOH (50 mL). To the stirred mixture was added DVB (5 mmol) along with H$_2$O$_2$ (15 mmol; 30% solution in water), which was added dropwise over 5 min. The reaction mixture was analyzed by GC-MS after 2 hr. The results are summarized in Table II.

Epoxidation Example 4

In this example, a high yield of DVBDO was obtained with 1.2 equivalents of hydrogen peroxide in a mixed solvent. The reaction was carried out as described in Epoxidation Example 3 but instead of using 1.5 equivalents of H$_2$O$_2$, 1.2 equivalents of H$_2$O$_2$ was used. The results are summarized in Table II.

Epoxidation Example 5

In this example, a high yield of DVBDO was obtained with 1.05 equivalents of hydrogen peroxide in a mixed solvent.

The reaction was carried out as described in Epoxidation Example 3 but instead of using 1.5 equivalents of $H_2O_2$, 1.05 equivalents of $H_2O_2$ was used. The results are summarized in Table II.

TABLE II

Results of DVBDO Formation as a Function of $H_2O_2$ Equivalents

| Example | Equivalents of $H_2O_2$ | Time (hr) | % Conversion of DVB | GC Area % DVBMO | GC Area % DVBDO | GC Area % By-product |
|---|---|---|---|---|---|---|
| Epoxidation 3 | 1.5 | 2 | 100 | 0 | 92.9 | 7.1 |
| Epoxidation 4 | 1.2 | 2 | 100 | 0 | 92.4 | 7.6 |
| Epoxidation 5 | 1.05 | 2 | 100 | 2.9 | 89.5 | 7.6 |

Epoxidation Example 3-5 illustrate that the use of the mixed solvent composed of approximately ⅓ $CH_2Cl_2$ and ⅔ t-amylOH allows for yields of DVBDO greater than 77% to be obtained when using less than 2 equivalents of $H_2O_2$ per vinyl group of DVB. A 92.4% yield of DVBDO was obtained when using just 1.2 equivalents of $H_2O_2$.

Epoxidation Example 6

High Yield of DVBDO Using 4-OMe-$H_2$Pydic $FeCl_3.6H_2O$ (16.9 mg, 0.0625 mmol) and the substituted 4-OMe-$H_2$Pydic (0.0625 mmol) were charged into a 50 mL round bottomed flask and MeOH (10 mL) was added. The mixture was stirred for 2 min to afford a pale yellow solution. Diisopropylamine (12.7 mg, 0.125 mmol) was added dropwise over 30 s and the mixture was placed in a 50° C. oil bath for 30 min. The solvent was removed under reduced pressure to afford a yellow residue. It was dissolved in $CH_2Cl_2$ (12.5 mL) and t-amylOH (25 mL). To the stirred mixture DVB (2.5 mmol) was added along with $H_2O_2$ (6 mmol as a 30% solution in water), which was added dropwise over 5 min. The reaction mixture was analyzed by GC-MS after 1 hr (see Table III).

Epoxidation Example 6 illustrates that the substituted $H_2$Pydic ligands can provide yields of DVBDO greater than 77%. For example, the 4-methoxy substituted ligands 4-OMe-$H_2$Pydic affords a 94% yield of DVBDO. This expands the scope of $H_2$Pydic ligands that can be used.

Epoxidation Example 7

High Yield of DVBDO Using 60% $H_2O_2$ with an Fe Loading of 1.25 mol %

$FeCl_3.6H_2O$ (33.8 mg, 0.125 mmol) and $H_2$Pydic (20.9 mg, 0.125 mmol) were charged into a 50 mL round bottomed flask and MeOH (20 mL) was added. The mixture was stirred for 2 min to afford a pale yellow solution. Diisopropylamine (25.3 mg, 0.250 mmol) was added dropwise over 30 s and the mixture was placed in a 50° C. oil bath for 30 min A 10 mL aliquot was removed from the sample and set aside for later use in Epoxidation Example 8. The solvent was removed from the remaining sample under reduced pressure to afford a yellow residue. The residue was dissolved in $CH_2Cl_2$ (25 mL) and t-amylOH (50 mL) and DVB (5 mmol) was added which afforded a 1.25 mol % loading of Fe. To the stirred mixture $H_2O_2$ (12 mmol, 60% in water) was added dropwise over 5 min. The reaction mixture was analyzed by GC-MS after 2 hr. The results are summarized in Table IV.

Comparative Epoxidation Example C

The reaction was carried out as described in Epoxidation Example 7 but 30% $H_2O_2$ was used instead of using 60% $H_2O_2$. The results are summarized in Table IV.

Epoxidation Example 8

In this example, a high yield of DVBDO was obtained using 60% $H_2O_2$ with an Fe loading of 0.625 mol %. A 5 mL aliquot was taken from the 10 mL aliquot set aside from Epoxidation Example 7. The solvent was removed from the remaining sample under reduced pressure to afford a yellow

TABLE III

GC-Area Yields of DVBMO and DVBDO Using 4-OMe—$H_2$Pydic

| Example | Ligand | Time, min | % Conversion of DVB | GC Area % DVBMO | GC Area % DVBDO | GC Area % By-product |
|---|---|---|---|---|---|---|
| Epoxidation 6 | (4-OMe-H₂Pydic structure) | 60 | 100 | 0 | 94.0 | 6.0 | residue. The residue was dissolved in $CH_2Cl_2$ (25 mL) and t-amylOH (50 mL) and DVB (5 mmol) was added, which afforded a 0.625 mol % loading of Fe. To the stirred mixture $H_2O_2$ (12 mmol, 60% in water) was added dropwise over 5 min. The reaction mixture was analyzed by GC-MS after 2 hr. The results are summarized in Table IV.

Comparative Epoxidation Example D

The reaction was carried out as described in Epoxidation Example 8 but 30% $H_2O_2$ was used instead of using 60% $H_2O_2$. The results are summarized in Table IV.

TABLE IV

GC-Area Yields of DVBMO and DVBDO

| Example | Catalyst (mol %) | $H_2O_2$ Conc. | Time (hr) | % Conversion of DVB | GC Area % DVBMO | GC Area % DVBDO | GC Area % By-product |
|---|---|---|---|---|---|---|---|
| Epoxidation 7 | 1.25 | 60% | 2 | 100 | 0 | 93.7 | 6.3 |
| Comparative C | 1.25 | 30% | 2 | 100 | 2.2 | 94.9 | 2.9 |
| Epoxidation 8 | 0.625 | 60% | 2 | 100 | 6.5 | 85.7 | 7.8 |
| Comparative D | 0.625 | 30% | 2 | 92 | 54.8 | 34.6 | 2.6 |

Epoxidation Examples 7-8 illustrate that the use of more concentrated $H_2O_2$ allows for higher yields of DVBDO to be obtained. For example, at an Fe loading of 0.625 mol % the yield of DVBDO is 34.6% with 54.8% of DVBMO remaining when 30% $H_2O_2$ is used. However, when 60% $H_2O_2$ is used the yield of DVBDO is 85.7% with just 6.5% DVBMO. Also, at a Fe loading of 1.25 mol % the use of 60% $H_2O_2$ allowed for completed conversion of DVBMO. The increased yield of DVBDO using more concentrated $H_2O_2$ is not obvious or expected.

Epoxidation Example 9

[(PydicFe(OMe)Cl)$_2$]2[NH$_2$(isopropyl)$_2$] and 10 mol % Addition of Diisopropylamine HCl

[(PydicFe(OMe)Cl)$_2$]2[NH$_2$(isopropyl)$_2$] (0.0625 mmol or 0.125 mmol of Fe) was added to 100 mL round bottom flask containing $CH_2Cl_2$ (25 mL) and t-amylOH (50 mL). Diisopropylamine HCl (68.8 mg; 0.5 mmol) was added and the mixture was stirred for 30 min. DVB (5 mmol) was added along with $H_2O_2$ (12 mmol as a 30% solution in water), which was added dropwise over 5 min. The reaction mixture was analyzed by GC-MS after 2 hr. The results are in Table V.

Epoxidation Example 10

In this example, [(PydicFe(OMe)Cl)$_2$]2[NH$_2$(isopropyl)$_2$] and 5 mol % addition of diisopropylamine HCl was used. The reaction was carried out as described in Epoxidation Example 9 but 5 mol % of diisopropylamine HCl (34.4 mg; 0.25 mmol) was added instead of 10 mol %. The results are summarized in Table V.

Epoxidation Example 11

In this example, [(PydicFe(OMe)Cl)$_2$]2[NH$_2$(isopropyl)$_2$] and 2.5 mol % addition of diisopropylamine HCl was used. The reaction was carried out as described in Epoxidation Example 9 but 2.5 mol % of diisopropylamine HCl (17.2 mg; 0.125 mmol) was added instead of 10 mol %. The results are summarized in Table V.

Comparative Epoxidation Example E

The reaction was carried out as described in Epoxidation Example 9 but no diisopropylamine HCl was added. The results are summarized in Table V.

TABLE V

GC-Area yields of DVBMO and DVBDO Using [(PydicFe(OMe)Cl)$_2$]2[NH$_2$(isopropyl)$_2$] and Diisopropylamine HCl

| Example | Diisopropylamine HCl (mol %) | Time (hr) | % Conversion of DVB | GC Area % DVBMO | GC Area % DVBDO | GC Area % By-product |
|---|---|---|---|---|---|---|
| Comparative E | 0 | 2 | 79.4 | 45.7 | 23.1 | 10.7 |
| Epoxidation 11 | 2.5 | 2 | 99 | 22.4 | 66.5 | 10.1 |
| Epoxidation 10 | 5.0 | 2 | 99.1 | 22.3 | 66.7 | 10 |
| Epoxidation 9 | 10.0 | 2 | 99.6 | 17.2 | 71.6 | 10.8 |

Epoxidation Example 12

PydicFeCl(OH$_2$)$_2$ and 10 mol % Addition of Diisopropylamine HCl

PydicFeCl(OH$_2$)$_2$ (0.125 mmol) was added to 100 mL round bottom flask containing $CH_2Cl_2$ (25 mL) and t-amylOH (50 mL). To this mixture was added diisopropylamine HCl (68.8 mg, 0.5 mol). The mixture was stirred for 30 min and DVB (5 mmol) was added. To the stirred mixture, $H_2O_2$ (12 mmol as a 30% solution in water) was added dropwise over 5 min and the reaction mixture was analyzed by GC-MS after 2 hr. The results are in Table VI.

Epoxidation Example 13

In this example, PydicFeCl(OH$_2$)$_2$ and 5 mol % addition of diisopropylamine HCl was used. The reaction was carried out as described in Epoxidation Example 12 but mol % of diisopropylamine HCl (34.4 mg; 0.25 mmol) was added instead of 10 mol %. The results are summarized in Table VI.

Epoxidation Example 14

In this example, PydicFeCl(OH$_2$)$_2$ and 2.5 mol % addition of diisopropylamine HCl was used. The reaction was carried out as described in Epoxidation Example 12 but 2.5 mol % of diisopropylamine HCl (17.2 mg; 0.125 mmol) was added instead of 10 mol %. The results are summarized in Table VI.

Comparative Epoxidation Example F

The reaction was carried out as described in Epoxidation Example 12 but no diisopropylamine HCl was added. The results are summarized in Table VI.

TABLE VI

GC-area Yields of DVBMO and DVBDO Using PydicFeCl(OH$_2$)$_2$ and Diisopropylamine HCl

| Example | Diisopropylamine HCl (mol %) | Time (hr) | % Conversion of DVB | GC Area % DVBMO | GC Area % DVBDO | GC Area % By-product |
|---|---|---|---|---|---|---|
| Comparative F | 0 | 2 | 11.5 | 7.1 | 4.4 | 0 |
| Epoxidation 14 | 2.5 | 2 | 99.2 | 19 | 70.8 | 9.4 |
| Epoxidation 13 | 5.0 | 2 | 100 | 4.3 | 86 | 9.7 |
| Epoxidation 12 | 10.0 | 2 | 100 | 1 | 87.3 | 11.5 |

Epoxidation Example 15

High Yield of DVBDO Using In Situ Generated Catalyst (0.31 mol % Fe), 60% H$_2$O$_2$, and Added Diisopropylamine HCl FeCl$_3$.6H$_2$O (33.8 mg, 0.125 mmol) and H$_2$Pydic (20.9 mg, 0.125 mmol) were charged into a 50 mL round bottomed flask and MeOH (20.0 mL) was added. The mixture was stirred for 2 min to afford a pale yellow solution. Diisopropylamine (25.3 mg, 0.250 mmol) was added dropwise over 30 s and the mixture was placed in a 50° C. oil bath for 30 min. The solvent was allowed to cool to room temp and a 2.50 mL aliquot was removed. The aliquot was placed in a 100 mL round bottom flask and the solvent was removed under reduced pressure to afford a yellow residue. Diisopropylamine HCl (21.3 mg, 0.156 mmol) was added to the residue and the mixture was dissolved in CH$_2$Cl$_2$ (25 mL) and t-amylOH (50 mL). To the stirred mixture, DVB (5 mmol) was added along with 60% H$_2$O$_2$ (12 mmol), which was added dropwise over 5 min. The reaction mixture was analyzed by GC-MS after 2 hr. The yield is in Table VII.

Comparative Epoxidation Example G

The reaction was carried out as described in Epoxidation Example 15 but 1.55 mol % of diisopropylamine HCl (10.65 mg; 0.078 mmol) was added instead of 3.1 mol %. The results are summarized in Table VII.

Comparative Epoxidation Example H

The reaction was carried out as described in Epoxidation Example 15 but no diisopropylamine HCl was added instead of 3.1 mol %. The results are summarized in Table VII.

TABLE VII

GC-Area Yields of DVBMO and DVBDO Using in situ Generated Catalyst and Diisopropylamine HCl

| Examples | Diisopropylamine HCl | Time (hr) | % Conversion of DVB | % DVBMO | % DVBDO | % By-product |
|---|---|---|---|---|---|---|
| Comparative G | 0 equiv | 2 | 95.9 | 52.4 | 41.1 | 2.4 |
| Comparative H | 5 equiv | 2 | 100 | 24.2 | 71.3 | 4.5 |
| Epoxidation 15 | 10 equiv | 2 | 100 | 9.4 | 85.6 | 5.0 |

Epoxidation Examples 9-15 illustrate that the yield of DVBDO is increased when diisopropylamine HCl is added to the reaction mixture. In Epoxidation Example 11 the yield of DVBDO is 23.1% when using the catalyst [(PydicFe(OMe)Cl)$_2$]2[NH$_2$(isopropyl)$_2$]. However, upon the addition of 10 mol % of diisopropylamine HCl (Example 9) the yield of DVBDO increases to 71.6%.

Epoxidation Example 14 further illustrates the increase in DVBDO yield upon addition of diisopropylamine HCl. For example, the yield of DVBDO is only 4.4% when using PydicFeCl(OH$_2$)$_2$ as a catalyst. However, upon the addition of 10 mol % of diisopropylamine HCl (Example 12) the yield of DVBDO increases to 87.3% with just 1% of DVBMO remaining.

In addition, Epoxidation Example 15 further illustrates the increase in DVBDO yield upon addition of diisopropylamine HCl. For example, the very low catalyst loading of 0.31 mol % Fe afforded a DVBDO yield of just 41.1% (Comparative Example G) However, upon adding 10 equivalents of diisopropylamine HCl (3.1 mol %) the yield of DVBDO more than doubled to 85.6%. This yield is greater than the 77% obtained in WO 2010-077483 A1, where the Fe loading was 5 mol %. It is quite remarkable that a higher yield of DVBDO could be obtained when using only 1/10 the amount of catalyst. The higher yield of DVBDO illustrates the importance of adding amine hydrogen halides to the reaction mixture.

Epoxidation Example 16

High Yield of DVBDO at a DVB Loading of 4% by Volume and an Fe Loading of 2.5 mol %

FeCl$_3$.6H$_2$O (135.2 mg, 0.5 mmol) and H$_2$Pydic (83.6 mg, 0.5 mmol) were charged into a 250 mL round bottomed flask and MeOH (75 mL) was added. The mixture was stirred for 2 min to afford a pale yellow solution. Diisopropylamine (101.2 mg, 1 mmol) was added dropwise over 1 min and the mixture was stirred in a 50° C. oil bath for 30 min. The solvent was removed under reduced pressure to afford a yellow residue that was dissolved in CH$_2$Cl$_2$ (21.9 mL) and t-amylOH (43.8 mL). Diisopropylamine HCl (342.5 mg, 2.5 mmol) was added and the mixture was stirred for 15 min. To the stirred mixture, DVB (20 mmol) was added and the mixture was cooled to 0° C. by placing the flask in an ice-bath. To the mixture, 60% H$_2$O$_2$ (48 mmol, 2.5 mL) was added dropwise via a syringe pump over 1 hr. The reaction mixture was analyzed by GC-MS after 2 hr. The results are in Table VIII.

TABLE VIII

GC-Area Yields of DVBMO and DVBDO as a Function of Catalyst Loading at a 4% Loading of DVB

| Example | Time (hr) | % Conversion of DVB | GC Area % DVBMO | GC Area % DVBDO | GC Area % By-product |
|---|---|---|---|---|---|
| Epoxidation 16 | 2 | 100 | 0 | 95.0 | 5.0 |

Epoxidation Example 16 illustrates that a high yield of DVBDO can be obtained with full conversion of DVBMO when using concentrated solutions of DVB. For example, as reported in WO 2010-077483 A1 a 77% yield of DVBDO was obtained, with a DVB loading of only 0.76% by volume. These solutions are very dilute solution, which means that large amounts of solvent have to be manipulated. However, it was found that the loading of DVB could be increased to 4% by volume and a 95% yield of DVBDO could be obtained without any remaining DVBMO. The conditions required for this transformation were the addition of 5 equivalents of diisopropylamine HCl (12.5 mol %), cooling the solution to 0° C., and that 60% $H_2O_2$ was added slowly via a syringe pump over 1 hr.

The invention claimed is:

1. A process for preparing a divinylarene dioxide comprising reacting (a) at least one divinylarene, (b) hydrogen peroxide, (c) at least one iron-containing catalyst, and (d) an excess of amine hydrogen halide, relative to the iron-containing catalyst, under conditions to form a divinylarene dioxide in higher than 77 percent yield.

2. The process of claim 1, wherein the divinylarene comprises divinylbenzene; and wherein the divinylarene dioxide formed comprises divinylbenzene dioxide.

3. The process of claim 1, wherein the reaction is carried out at a mole ratio of hydrogen peroxide:divinylarene of up to about 5:1.

4. The process of claim 1, wherein the iron-containing catalyst comprises an iron (Fe) salt and a chelating ligand.

5. The process of claim 4, wherein the chelating ligand comprises alkyl- or aryl-substituted formamidines; unsubstituted or alkyl-, aryl-, aralkyl-, halogen-, carboxylic acid-, amino-substituted N-heterocycles and amino acids, or mixtures thereof.

6. The process of claim 4 or claim 5, wherein the Fe salt comprises Fe(II) chloride or bromide or acetate, Fe(III) fluoride, chloride, bromide, acetate and the chelating ligand is imidazole, $H_2$Pydic, pyrazole, pyridine, oxazole, thiazole; histidine, or mixtures thereof.

7. The process of claim 1, wherein the loading of the iron-containing catalyst ranges from 0.001 mol % to 20 mol % of the divinylarene.

8. The process of claim 1, wherein the iron-containing catalyst is isolated or generated in-situ in the reaction mixture.

9. The process of claim 1, wherein the catalyst is immobilized on a solid support; and the solid support comprises zeolites, clays, silica, alumina, or polymers; or wherein the polymer solid support comprises, polyglycerol, polystyrene, polymethacrylates, dendrimers, or polyvinyl-pyridine.

10. The process of claim 1, wherein the amine hydrogen halide comprises hydrogen halide salts of aliphatic, arylalkyl or cycloaliphatic amines, amino acids, or mixtures thereof wherein the hydrogen halide component of the amine hydrogen halide salt comprises hydrogen fluoride, hydrogen chloride, hydrogen bromide, hydrogen iodide or mixtures thereof; and wherein the amine component of the amine hydrogen halide salt comprises propyl amine, isopropyl amine, diisopropylamine, benzyl amine, cyclohexylamine, histidine, or mixtures thereof.

11. The process of claim 1, wherein the loading of the amine hydrogen chloride ranges from 1 to 10 equivalents relative to the iron-containing catalyst.

12. The process of claim 1, wherein the reaction is carried out at a temperature within the range of from 0° C. to 80° C.

13. The process of claim 1, including a solvent; wherein the solvent comprises halogenated hydrocarbons, aromatic hydrocarbons, polar solvents, ethers, alcohols, fluorinated alcohols, ketones, or mixtures thereof; and wherein the concentration of the solvent ranges from 80 weight percent to 99 weight percent.

14. The process of claim 13, wherein the solvent comprises dichloromethane, dichloroethane, toluene, dimethyl formamide, acetonitrile, tetrahydrofuran, tert-amyl alcohol, tert-butanol, methanol, ethanol, trifluoroethanol, acetone, methyl-ethyl-ketone, or mixtures thereof.

* * * * *